United States Patent [19]

Pokorny

[11] Patent Number: 5,083,572
[45] Date of Patent: Jan. 28, 1992

[54] REMOVAL OF SECRETIONS FROM THE PREPUBERTAL VAGINA

[76] Inventor: Susan F. Pokorny, 1111 Hermann Dr., #21-D, Houston, Tex. 77004

[21] Appl. No.: 454,070

[22] Filed: Dec. 21, 1989

Related U.S. Application Data

[63] Continuation-in-part of Ser. No. 151,360, Feb. 2, 1988, abandoned.

[51] Int. Cl.⁵ .................. A61B 10/00; A61B 17/42
[52] U.S. Cl. .................................. 128/768; 128/760; 604/27; 604/28; 604/54; 604/55; 604/93; 604/330
[58] Field of Search ............... 128/749-759, 128/760, 763, 765, 768; 604/27, 28, 30, 35, 36-38, 43, 54, 55, 93, 128, 129, 330-331, 173

[56] References Cited

U.S. PATENT DOCUMENTS

| | | | |
|---|---|---|---|
| 3,065,749 | 11/1962 | Brass | 604/35 |
| 3,527,203 | 9/1970 | Gravelee | 128/750 |
| 3,606,878 | 10/1971 | Kellog | 128/753 |
| 3,626,928 | 12/1971 | Barringer et al. | 128/750 |
| 3,777,743 | 12/1973 | Binard et al. | 128/749 |
| 3,796,211 | 3/1974 | Kohl | 128/749 |
| 4,627,444 | 12/1986 | Brooker | 128/758 |
| 4,674,502 | 6/1987 | Imonti | 128/750 |
| 4,790,814 | 12/1988 | Fischl et al. | 604/55 |
| 4,911,704 | 3/1990 | Dixon | 604/55 |

FOREIGN PATENT DOCUMENTS 8103125  11/1981  World Int. Prop. O. .......... 128/752

OTHER PUBLICATIONS

Pokorny et al., "Atraumatic Removal of Secretions from the Prepubertal Vagina", Am. Journal OBGYN, vol. 156, No. 3, pp. 581-582 (Mar. 1987).

Capraro et al., "Instrument and Method", Obstetrics and Gynecology, vol. 37, No. 3, pp. 462-464 (Mar. 1971).

Altcheck, "Pediatric Vulvovaginitis", Jrn. of Reproductive Medicine, vol. 29, No. 6, pp. 359-375, (Jun. 1984).

Emans et al., Pediatric Adolescent Gynecology, Little, Brown and Co., Boston, (1982).

*Primary Examiner*—Lee S. Cohen
*Assistant Examiner*—K. M. Pfaffle
*Attorney, Agent, or Firm*—James F. Weiler

[57] ABSTRACT

Disclosed are methods of and apparatus for obtaining adequate vaginal secretions from the vaginas of prepubertal females for laboratory tests without causing iatrogenic damage to the genital tract and without frightening or causing trauma to the females. The apparatus comprises an inner flexible catheter having a passage within an outer flexible catheter, the catheters having fluid communicating sampling ports, the injection, aspiration, and withdrawal of fluids and secretions in or from a child being through the passage in the inner flexible catheter, the outer flexible catheter maintaining its shape in use effective to prevent the inner flexible catheter and hence the outer catheter from being forced or sucked against the child's vaginal walls during such injection of fluid, aspiration and withdrawal of vaginal fluid. The method describes the use of the apparatus in obtaining the fluids and secretions.

9 Claims, 1 Drawing Sheet

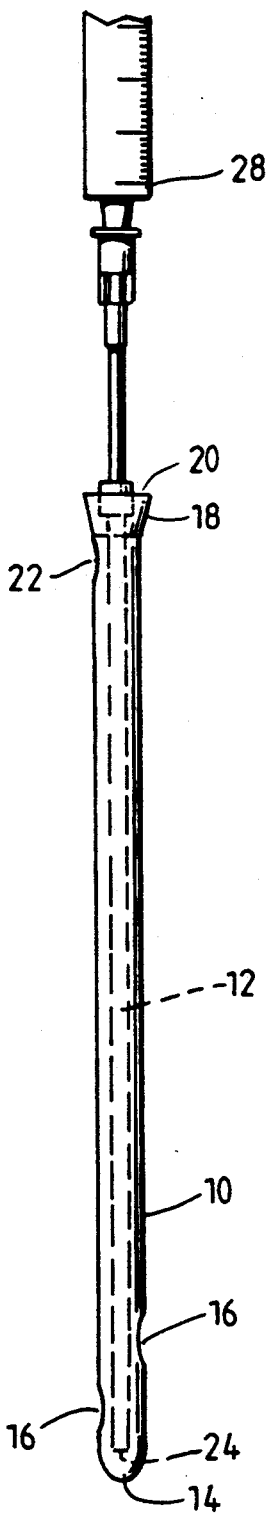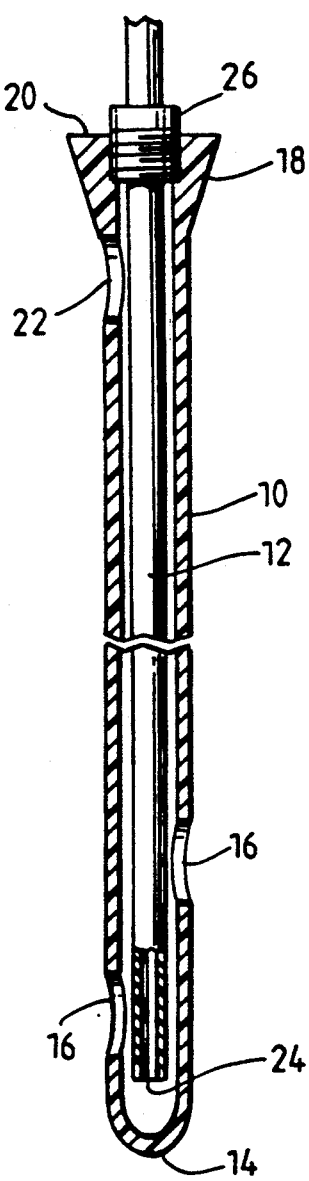

REMOVAL OF SECRETIONS FROM THE PREPUBERTAL VAGINA

CROSS REFERENCE TO RELATED APPLICATION

The present application is a continuation-in-part of U.S. application Ser. No. 151,360, filed Feb. 2, 1988, abandoned in favor of this application.

FIELD OF THE INVENTION

The present invention relates to obtaining adequate vaginal secretions from the vaginas of prepubertal females for laboratory tests.

BACKGROUND OF THE INVENTION

Anxiety is common among physicians who need to obtain secretions from the vagina of a prepubertal child. Because children rarely comply with these procedures, there is a chance of iatrogenic damage to the thin, delicate, unestrogenized mucosa of the genital tract. Furthermore, because these procedures can have long-lasting psychosocial effects, manipulation of the genital tract should be performed cautiously.

Techniques described in most textbooks for obtaining vaginal secretions are far from ideal. Altcheck, A. Pediatric vulvovaginitis. J. Reprod. Med. 29:359-375, 1984. Emans, S. J. and Goldstein, D. P. *Pediatric and Adolescent Gynecology.* Little, Brown and Company, Boston, 1982. p.47. They can be traumatic and yield only small amounts of material. Q-tips are abrasive to the unestrogenized mucosa and should not be used. Eye droppers, pipettes, and plastic cannulas are smooth and unabrasive, but can cause trauma due to inadvertent patient movement. Any single chambered tube or cannula placed in these small vaginas will be sucked against the vaginal wall when an effort is made to withdraw secretions, making the yield of material very small. Furthermore, the suction frequently alarms the child.

Many children with vulvovaginitis go through needless courses of creams and antibiotics because the infectious organism is never identified. Many children who have been sexually exploited have their story unsubstantiated because material for forensic rape kits and/or cultures is never obtained. Through the use of the present invention the management of children with these common pediatric gynecology problems will be improved.

SUMMARY OF THE INVENTION

The present invention is directed to an atraumatic method of and an apparatus for obtaining adequate vaginal secretions from the vagina of a prepubertal child. An outer flexible catheter having a smooth outer surface and a closed outer end insertable into the vagina has an inner flexible catheter removably fixed against axial movement in it through which diluting or washing solution is injected, aspirated, and withdrawn with secretions from the vagina. The outer catheter has at least one sampling opening or port proximate its outer end providing fluid communication between the vagina and its interior, and the inner catheter has at least one opening or sampling port, such as an open outer end, providing fluid communication between the inner and outer catheters and thereby with the vagina. The outer and inner catheters are flexible to accommodate movement of the child in use. The outer flexible catheter maintains its tubular shape in use and thus is effective to prevent the inner flexible catheter, and hence the outer catheter, from being sucked or forced against the vaginal wall when injection, aspirating fluid and withdrawing secretions as would be the case of any single chamber tube or cannula. This provides a satisfactory sample of vaginal secretions without trauma to the child. In the case of a single catheter, the yield of material from the vagina is very small when the catheter is sucked up against the vaginal wall, and this frequently alarms and causes trauma to the child.

Accordingly, it is an object of the present invention to provide an apparatus for and a method of obtaining adequate vaginal secretions from the vagina of a prepubertal child without iatrogenic damage to the mucosa of the genital tract and without frightening or causing trauma to the prepubertal child.

A further object of the present invention is the provision of an apparatus for atraumatic injection, aspiration and withdrawal of fluids and secretions in and from a vagina of a prepubertal child comprising an outer flexible catheter having a closed outer end insertable into the vagina with a sampling port adjacent its outer end, and an inner flexible catheter removably fixed against axial movement in the outer catheter and having a sampling port for flow of fluid between the inner and outer catheters and hence between the vagina and the interior of the inner catheter, the outer flexible catheter maintaining its tubular shape in use and thus being effective to prevent the inner flexible catheter and hence the outer catheter from being forced or sucked against the vaginal walls during the injection of fluid, aspiration, and withdrawal of vaginal fluid.

A still further object of the present invention is the provision of such an apparatus in which means are provided for connecting and sealing the inner and outer catheters proximate their inner ends.

A further object of the present invention is an atraumatic method of obtaining vaginal secretions from the vagina of a prepubertal child by inserting an outer flexible catheter having an inner flexible catheter disposed or insertable within it and withdrawing the secretions from the vagina in the inner flexible catheter while preventing the inner flexible catheter from being forced or sucked against the vaginal wall by the outer catheter to thereby obtain an adequate vaginal fluid sample without frightening or causing trauma to the child.

A further object of the present invention is the provision of such an atraumatic method in which fluid is injected, aspirated, and the fluid and vaginal secretions are withdrawn in the inner flexible catheter without the inner flexible catheter being forced or sucked against the vaginal wall.

A further object of the present invention is the provision of such apparatus and methods in which the inner flexible catheter can be removed from the outer flexible catheter while the outer flexible catheter is in place in the vagina for other sampling, such as inserting a small urethral swab in the outer flexible catheter for obtaining Chlamydia cultures, after vaginal washings for routine studies have been obtained, as previously mentioned.

Other and further objects, features, and advantages of the present invention appear throughout and are inherent therein.

U.S. Pat. No. 3,777,743 discloses an indometrical sampler made up of two tubes, one within the other, the outer tube being rigid, and the inner tube being a flexible sampling tube which is extended outwardly from the inner tube exposing a plurality of sampling ports 22 when collecting samples.

U.S. Pat. No. 2,460,473 discloses a catheter with an inner and outer passage, the inner passage carrying fluid into the body and the outer passage removing the fluid for irrigating and draining kidneys.

U.S. Pat. No. 4,036,322 discloses an aspiration device using a preloaded syringe to draw vacuum on a catheter after it is inserted.

*Obstetrics and Gynecology,* Volume 37, No. 3, March 1971, 462–464, Dr. Capraro, et al., describes an apparatus that is more flexible and therefore less traumatic than the inflexible medicine dropper previously advocated; however, there is no disclosure of an outer catheter and an inner catheter with its advantages.

BRIEF DESCRIPTION OF THE DRAWINGS

FIG. 1 is a view illustrating the outer catheter with the inner catheter in it and a syringe attached to the inner catheter.

FIG. 2 is a cross-sectional view illustrating the outer catheter with the inner catheter in it.

DESCRIPTION OF PREFERRED EMBODIMENTS

Referring to FIGS. 1 and 2, the apparatus of the invention is illustrated which includes the outer flexible catheter 10 and the inner flexible catheter 12 removably fixed against axial movement within it. The outer and inner flexible catheters 10 and 12 are tube shaped, as illustrated. The outer flexible catheter 10 has a smooth outer wall and is closed at its outer end 14 and has the sampling ports 16 proximate its outer end. If desired, a hub or flared portion 18 is provided at its inner end 20 for ease of handling and manipulation. Also, if desired, an opening 22 may be provided adjacent the hub or flared portion 18 which can be closed or covered, such as by the examiner's finger, in cases where fluid needs to be injected into a vagina under pressure.

The inner flexible catheter 12 is also tube shaped and has a sampling port 24 adjacent its outer end, here shown as the open end of the inner catheter 12, and it is removable fixed against axial movement in the outer catheter 10 by means of the connection 26 which also seals any space around the insertion site of the inner flexible catheter 12 into the outer flexible catheter 10. The inner flexible catheter is adapted to receive the syringe 28 for injection of fluid, aspiration of fluid, and removal of fluid from a vagina, not shown, through the inner catheter 12.

The connection 26 may be in the form of screw threads or a quick make up connection, such as a bayonette connection, a friction connection, or by other suitable means for securing and sealing the inner flexible catheter 12 in the outer flexible catheter 14 and preventing axial or sliding movement with respect to the outer flexible catheter 10.

The outer catheter 10 should be formed of a flexible smooth material or materials, have a smooth outer surface, and have the property of maintaining its tubular shape when inserted into the vagina and thus preventing it from bulging outwardly and forced or sucked against the vaginal wall by movement of the inner catheter 12 during use in obtaining vaginal secretions. For example, a size 12 catheter having a rounded outer end from Argyle, division of Sherwood Medical, St. Louis, Mo., can be used to form the flexible outer catheter 10. As previously mentioned, the outer catheter is formed from flexible material having strength sufficient to prevent a change of shape or bulging of portions when in use, and can be transparent or opaque.

The inner flexible catheter can be formed from flexible tubing, such as butterfly tubing marketed by Abbott Hospitals Inc., North Chicago, Ill.

It is important that the outer 10 and inner 12 catheters be flexible to accommodate movements of the child when inserted into her vagina. The catheters should be flexible enough to indent under hand pressure to accommodate such movements.

In general, the outer catheter 10 and inner catheter 12 can be formed of flexible plastic compatible for use, such as used for bladder catheters.

Good results have been obtained by having the outer flexible catheter 10 8 to 10 cm in length, and 4 to 5 mm outside diameter with 1 mm thick walls, and the inner flexible catheter 12 8 cm in length, and 2 to 3 mm outside diameter with 0.5 mm thick walls. Oval sampling ports having a longitudinal axis of 1 cm are disposed 1.0 to 1.5 cm from the outer end of the outer catheter 10.

In use, the apparatus is assembled as illustrated in FIG. 2 and is gently inserted into the child's vagina. Once the apparatus is inserted, the examiner can alternately inject and aspirate a small amount of diluting or washing fluid with the syringe 28, the fluid flowing through the flexible inner catheter 12 and into and out of the vagina through the sampling port 16 of the inner catheter 10 and the sampling ports 16 of the outer flexible catheter 10 to obtain a good admixture of material from the vagina, and after drawing the material back into the syringe 28 through the inner flexible catheter 12, the entire apparatus can be quickly withdrawn. Depending upon the situation, the examiner can obtain from one atraumatic procedure enough fluid for the following: an examination for sperm particles and acid phosphates, a gram stain, a gonorrhea culture, a Chlamydia culture, a "wet mount," and other cultures as needed. Advantageously, the inner flexible catheter 12 can be removed from the outer flexible catheter 10 either when the entire catheter is removed or with the outer flexible catheter 10 in place, and a urethral swab, not shown can be inserted through the already in place outer flexible catheter 10 for obtaining Chlamydia cultures, after vaginal washings for routine studies have been obtained, as described above. This is significant because a richer cell sample is obtained from the vagina of young girls by the use of the swab since Chlamydia is an intracellular organism and in some cases enough positive vaginal Chlamydia cultures are not obtained when using the "wash" method alone.

The present invention, therefore, is well suited and adapted to attain the objects and ends and has the advantages and features mentioned as well as others inherent therein.

While presently preferred embodiments of the invention have been given for the purposes of disclosure, changes and additional applications will suggest themselves to those skilled in the art to which the invention is directed as defined by the scope of the appended claims.

What is claimed is:

1. Apparatus for atraumatic injection, aspiration, and withdrawal of fluids and secretions in a vagina of a prepubertal child comprising, an outer flexible catheter having a proximal end and having a tubular shape, a smooth outer surface and a closed outer end insertable into the vagina and having sampling port means proximate the outer end providing fluid communication between the vagina and the outer flexible cather's interior, and an inner flexible catheter having a proximal end and having an internal passage removably fixed against axial movement in the outer catheter having sampling port means providing fluid communication between the interior of the outer flexible catheter and the internal passage of the inner flexible catheter, the outer flexible catheter being formed of a material which maintains its tubular shape when inserted into the vagina and is effective to prevent the outer flexible catheter to bulge outwardly and be forced or sucked against the vaginal wall by movement of the inner flexible catheter and the fluids and secretions during the injection, aspiration, and removal of fluid and secretions from the vagina through the internal passage in the inner flexible catheter, the inner and outer flexible catheters flexing upon movement of the child when in her vagina.

2. The apparatus of claim 1 including
means for connecting a syringe to the inner catheter.

3. The apparatus of claim 1 where,
the outer catheter has an opening adjacent its proximal end closable by an operator during sampling.

4. The apparatus of claim 1 including,
seal means for sealing the inner and outer flexible catheters adjacent to their proximal ends.

5. The apparatus of claim 1 including,
seal means for sealing the inner and outer flexible catheters adjacent to their proximal ends,
the outer catheter having an opening closable by an operator downstream of the sealing means for injecting the fluid through the sampling port means of the inner and the outer flexible catheters under pressure into the vagina when the opening is closed.

6. A method of obtaining secretions from a vagina of a prepubertal child comprising,
inserting the apparatus of claim 5 into the vagina,
introducing fluid into the passage in the inner flexible catheter closing the opening thereby injecting the fluid under pressure through the passage and sampling port means in the inner flexible catheter, then into the outer flexible catheter and through its sampling port means and then withdrawing the fluid and the vaginal secretions from the vagina through the sampling port means in the outer flexible catheter and then through the sampling port means of the inner flexible catheter and into, through, and out of its passage.

7. A method of obtaining secretions from a vagina of a prepubertal child comprising,
inserting the apparatus of claim 5 into the vagina,
introducing fluid into the passage in the inner flexible catheter, closing the opening thereby injecting the fluid under pressure through the passage and out the sampling port means in the inner flexible catheter into the outer flexible catheter and then through the sampling port means in the outer flexible catheter into the vagina,
aspirating the fluid int he passage under pressure by maintaining the opening closed, and
withdrawing the fluid and the vaginal secretions from the vagina through the sampling port means in the outer and the inner flexible catheters and then through the passage in the inner flexible catheter.

8. An atraumatic method of obtaining secretions from a vagina of a prepubertal child comprising,
inserting the apparatus of claims 1, 2, 3, 4 or 5 into the vagina,
injecting fluid through the passage in the inner flexible catheter out its sampling port means into the outer flexible catheter and then through the sampling port means in the outer flexible catheter into the vagina,
withdrawing the injecting fluid and vaginal secretions from the vagina through the sampling port means in the outer flexible catheter and then through the sampling port means in the inner flexible catheter into, through, and out of the inner flexible passage.

9. A method of obtaining secretions from a vagina of a prepubertal child comprising,
inserting the apparatus of claims 1, 2, 3, 4 or 5 into the vagina,
introducing fluid into the vagina through the passage in the inner flexible catheter through its sampling port means into the outer flexible catheter and through its sampling port means,
aspirating the fluid in the vagina thereby mixing vaginal secretions in the vagina with the fluid, and
withdrawing the fluid and the vaginal secretions from the vagina through the sampling port means in the outer and the inner flexible catheters and then into, through, and out of the passage in the inner flexible catheter.

* * * * *

UNITED STATES PATENT AND TRADEMARK OFFICE
CERTIFICATE OF CORRECTION

PATENT NO. : 5,083,572
DATED : January 28, 1992
INVENTOR(S) : Suan F. Pokorny

It is certified that error appears in the above-indentified patent and that said Letters Patent is hereby corrected as shown below:

On title page, add item [30] to read as follows:

Foreign Application Priority Data

Feb. 4, 1987 (GB)    United Kingdom .........................8702509

Signed and Sealed this

Twenty-seventh Day of September, 1994

Attest:

BRUCE LEHMAN

*Attesting Officer*     *Commissioner of Patents and Trademarks*